United States Patent
Ohtake et al.

(10) Patent No.: US 7,973,125 B2
(45) Date of Patent: Jul. 5, 2011

(54) METHOD OF EVALUATING POLYMIDE DISSOLUTION RATE, METHOD OF PRODUCING POLYMIDE, AND POLYMIDE OBTAINED USING SAME METHODS

(75) Inventors: Gouki Ohtake, Hitachi (JP); Kazuhiro Ishibashi, Hitachi (JP); Keijirou Honda, Hitachi (JP); Naoki Okuda, Hitachi (JP); Nori Sasaki, Hitachi (JP)

(73) Assignee: Hitachi Chemical Co., Ltd., Tokyo (JP)

(*) Notice: Subject to any disclaimer, the term of this patent is extended or adjusted under 35 U.S.C. 154(b) by 747 days.

(21) Appl. No.: 11/575,779

(22) PCT Filed: Mar. 31, 2006

(86) PCT No.: PCT/JP2006/306863
§ 371 (c)(1),
(2), (4) Date: Mar. 22, 2007

(87) PCT Pub. No.: WO2006/106934
PCT Pub. Date: Oct. 12, 2006

(65) Prior Publication Data
US 2009/0192287 A1    Jul. 30, 2009

(30) Foreign Application Priority Data
Mar. 31, 2005 (JP) ................................ 2005-102245

(51) Int. Cl.
C08G 69/26  (2006.01)
(52) U.S. Cl. ........................................ 528/335; 356/301
(58) Field of Classification Search .................. 528/335; 356/301
See application file for complete search history.

(56) References Cited

U.S. PATENT DOCUMENTS
| | | | |
|---|---|---|---|
| 2004/0161711 A1* | 8/2004 | Rushkin et al. | 430/325 |
| 2006/0009573 A1* | 1/2006 | Van Den Abbeele et al. | 524/811 |

FOREIGN PATENT DOCUMENTS
| JP | 10233567 | * | 9/1998 |
|---|---|---|---|
| JP | 10-318923 | | 12/1998 |
| JP | 2000-516342 | | 12/2000 |
| JP | 2001-508354 | | 6/2001 |
| JP | 2003-236870 | | 8/2003 |
| JP | 2003-246870 | | 9/2003 |
| JP | 2005-507456 | | 3/2005 |
| JP | 2005085957 | * | 3/2005 |

(Continued)

OTHER PUBLICATIONS
Japanese Official Action issued Feb. 16, 2010, for Application No. 2007-511178.

(Continued)

*Primary Examiner* — Randy Gulakowski
*Assistant Examiner* — Shane Fang
(74) *Attorney, Agent, or Firm* — Antonelli, Terry, Stout & Kraus, LLP.

(57) ABSTRACT

A method of evaluating the dissolution rate of a polyimide by Raman spectroscopy, wherein the Raman spectral intensity I(a) of imide groups contained within the polyimide is measured, and I(a) is then compared with the Raman spectral intensity I(b) of imide groups contained within a polyimide with a known dissolution rate. The polyimides are preferably obtained using an aromatic tetracarboxylic dianhydride and/or an aromatic diamine.

22 Claims, 8 Drawing Sheets

FOREIGN PATENT DOCUMENTS

| | | |
|---|---|---|
| JP | 2005-102245 | 4/2005 |
| WO | WO 98/08066 | 2/1998 |
| WO | WO 98/29787 | 7/1998 |

OTHER PUBLICATIONS

Extended European Search Report, dated Oct. 13, 2010, including the Supplementary European Search Report and an European Search Opinion, for EP Application No. 06730811.4-2204/1788380 PCT/JP2006306863.

J. F. Aust, et al., "Fourier transform Raman spectroscopic studies of a polyimide curing reaction" *Analytica Chimica Acta*, 293 (Jul. 20, 1994), pp. 119-128.

S. F. Parker, "The application of vibrational spectroscopy to the study of polyimides and their composites", *Vibrational Spectroscopy*, 3 (Apr. 24, 1992), pp. 87-104.

J. B. Cooper, "Chemometric analysis of Raman spectroscopic data for process control applications", *Chemometrics and Intelligent Laboratory Systems*, 46 (Mar. 15, 1999), pp. 231-247.

H-R Lee, et al., "Characterization and Dissolution Studies of a Benzophenone-Containing Organic-Soluble Polyimide", *Macromolecules*, 23 (Jan. 22, 1990), pp. 502-509.

\* cited by examiner

METHOD OF EVALUATING POLYMIDE DISSOLUTION RATE, METHOD OF PRODUCING POLYMIDE, AND POLYMIDE OBTAINED USING SAME METHODS

TECHNICAL FIELD

The present invention relates to a method of evaluating a polyimide dissolution rate, a method of producing a polyimide, and a polyimide obtained using these methods.

BACKGROUND ART

Polyimides exhibit excellent heat resistance and mechanical properties, can be readily formed into films, and can be subjected to surface flattening, and are consequently widely used as surface protective films and interlayer insulation films and the like for semiconductor elements. When such polyimides are used as surface protective films or interlayer insulation films or the like, processes for the formation of through-holes and the like are mainly conducted by etching processes using positive photoresists.

During such processes, the polyimide dissolution rate (etching rate) is an important property in terms of controlling the size of the polyimide portion removed during the etching process. In highly automated semiconductor production processes, fluctuations in the polyimide dissolution rate can have a significant effect on falls in productivity levels and the generation of defects. Accordingly, a method of simply evaluating the polyimide dissolution rate, and a method that enables this evaluation to be conducted on-line or in-line where necessary, are sought. Examples of known methods of evaluating properties include a method of forecasting the properties of product materials, and a method of ascertaining the chemical structural components within a composition (for example, see Japanese translation of PCT international application No. 2000-516342 and Japanese translation of PCT international application No. 2001-508354).

DISCLOSURE OF INVENTION

Conventionally, the dissolution rate has been measured by actually conducting dissolution of the polyimide film. An example of the sequence employed in a method of measuring the dissolution rate is described below.

(1) Apply the polyimide to a Si wafer, (2) cure the polyimide film, (3) measure the film thickness, (4) conduct etching (dissolution) for a fixed period, and then wash and dry the film, (5) measure the residual film thickness, (6) calculate the dissolution rate from the reduction in polyimide film thickness and the etching time. This type of measurement of the dissolution rate suffers from numerous problems, including requiring considerable time for measurement, requiring skill to conduct the measurement, and suffering from considerable fluctuation in measurement results depending on the individual conducting the measurement. Because this type of method of measuring the dissolution rate is overly complex, automated measurement using a machine or the like is impossible, and because of the time required for measurement, the method cannot be employed within on-line or in-line inspections.

Furthermore, with conventional methods of producing polyimides, obtaining a polyimide of uniform quality in a stable manner is very difficult.

Accordingly, an object of the present invention is to replace the method of measuring the dissolution rate by conducting an actual dissolution of the polyimide, and provide a simple method of evaluating the dissolution rate, and a method of producing a polyimide that uses such an evaluation method. Furthermore, another object of the present invention is to provide a simple method of producing a polyimide that enables the production of a desired polyimide. Yet another object of the present invention is to provide polyimides obtained using these production methods and semiconductor devices that use these polyimides.

Polyimides are generally produced by a method in which a tetracarboxylic dianhydride and a diamine are reacted together in a solvent to generate a polyamic acid, and this polyamic acid is then subjected to a cyclodehydration to generate the imide groups. As a result of intensive investigation, the inventors of the present invention discovered that during the process of generating the polyimide from the polyamic acid, the solubility of the polyimide (polyamic acid) within the solution varies, and that consequently, an evaluation of the dissolution rate that involves measuring the Raman spectral intensity of imide groups contained within the polyimide could be employed as a substitute to the conventional measurement of dissolution rate, and they were therefore able to complete the present invention.

In other words, the present invention is as described below.

The present invention relates to a method of evaluating the dissolution rate of a polyimide by Raman spectroscopy, wherein the Raman spectral intensity $I(a)$ of imide groups contained within the polyimide is measured, and $I(a)$ is compared with the Raman spectral intensity $I(b)$ of imide groups contained within a polyimide with a known dissolution rate.

The above polyimides are preferably obtained using an aromatic tetracarboxylic dianhydride and/or an aromatic diamine.

In the above method of evaluating the dissolution rate, the intensity ratio $I(a_1)/I(a_2)$ between the Raman spectral intensity $I(a_1)$ of imide groups and the Raman spectral intensity $I(a_2)$ of aromatic rings contained within the polyimide can also be compared with the intensity ratio $I(b_1)/I(b_2)$ between the Raman spectral intensity $I(b_1)$ of imide groups and the Raman spectral intensity $I(b_2)$ of aromatic rings contained within a polyimide with a known dissolution rate. In addition, in the above method of evaluating the dissolution rate, the correlation equation between the intensity ratio $I(b_1)/I(b_2)$ between the Raman spectral intensity $I(b_1)$ of imide groups and the Raman spectral intensity $I(b_2)$ of aromatic rings contained within a polyimide with a known dissolution rate, and the dissolution rate of that polyimide can be used as a calibration curve. The aromatic rings are preferably benzene rings.

In the above method of evaluating the dissolution rate, the Raman spectral intensity of carboxyl groups can also be measured instead of the Raman spectral intensity of imide groups.

Furthermore, the present invention also relates to a method of producing a polyimide, wherein an evaluation of the dissolution rate is made using the above method of evaluating the dissolution rate, and reaction control is then conducted on the basis of the result of that evaluation of the dissolution rate. The evaluation of the dissolution rate can be conducted off-line, on-line or in-line, but is preferably conducted either on-line or in-line.

The above production method preferably comprises (1) a process of obtaining a polyamic acid using a tetracarboxylic dianhydride and a diamine, and (2) a process of obtaining a polyimide by heating the polyamic acid, wherein the dissolution rate evaluation is conducted during the process (2), and the heating temperature and/or the heating time can then be controlled on the basis of the result of the dissolution rate evaluation. Moreover, an evaluation of the polyimide viscosity may also be conducted during the process (2), and the heating temperature and/or the heating time can then be controlled on the basis of the results of the dissolution rate evaluation and the viscosity evaluation.

In the above production method, the Raman spectral intensity of carboxyl groups could also be measured instead of the Raman spectral intensity of imide groups.

Furthermore, the present invention also relates to a method of producing a polyimide, wherein the Raman spectral intensity of imide groups and/or carboxyl groups contained within the polyimide is measured by Raman spectroscopy, and reaction control is then conducted on the basis of the result of the measurement. Moreover, the viscosity of the polyimide may also be measured, and reaction control can then be conducted on the basis of the result of the measurement of the Raman spectral intensity of imide groups and/or carboxyl groups and the result of the measurement of the viscosity. Measurement of the Raman spectral intensity can be conducted off-line, on-line or in-line, but is preferably conducted either on-line or in-line.

Furthermore, the present invention also relates to a polyimide obtained by conducting an evaluation using the above method of evaluating the dissolution rate, to polyimides obtained using the above methods of producing a polyimide, and to semiconductor devices that use these polyimides.

The present disclosure relates to subject matter contained in Japanese Patent Application No. 2005-102245 filed on Mar. 31, 2005, the disclosure of which is expressly incorporated herein by reference in its entirety.

BEST MODE FOR CARRYING OUT THE INVENTION

Figure 1:
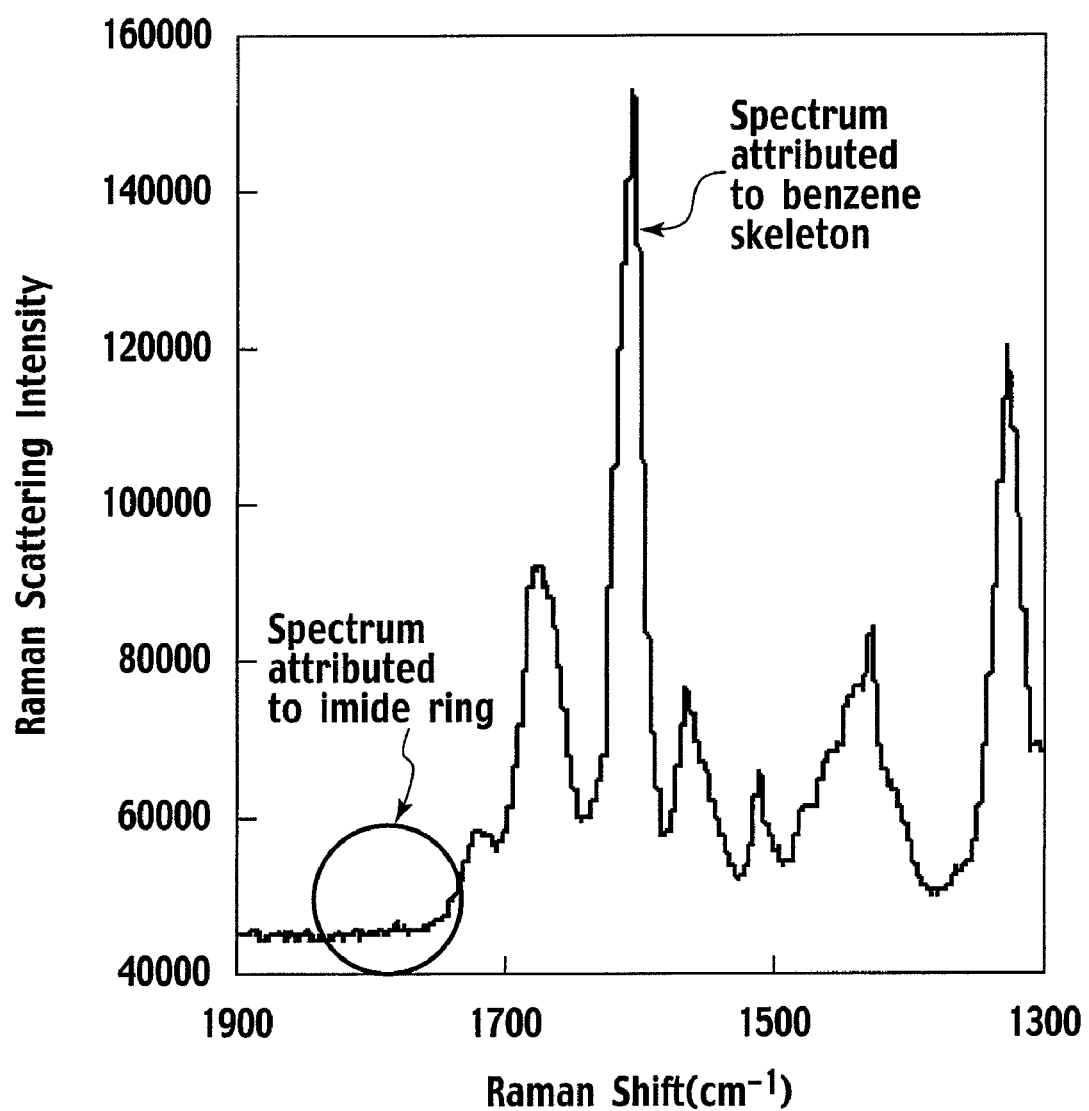
FIG. 1 is a diagram showing an example of a Raman spectrum of a polyamic acid.

In a method of evaluating the dissolution rate of a polyimide by Raman spectroscopy according to the present invention, the Raman spectral intensity $I(a)$ of the imide groups within the polyimide is measured, and $I(a)$ is then compared with the Raman spectral intensity $I(b)$ of imide groups within a polyimide with a known dissolution rate. FIG. 1 shows a Raman spectrum for a polyimide, measured across a wave number range of 1,300 to 1,900 $cm^{-1}$.

A polyimide can be obtained by a polycondensation of a tetracarboxylic dianhydride and a diamine. The polyimide is usually obtained by first polymerizing a tetracarboxylic dianhydride and a diamine to yield a polyimide precursor (a polyamic acid) (process (1) mentioned below), and subsequently subjecting the polyamic acid to a cyclodehydration (an imidization reaction, or a reaction that generates an imide group) (process (2) mentioned below). In the present invention, when the term "polyimide" is used, the "polyimide" may include a polyamic acid that has undergone partial imidization. Furthermore, when the term "polyamic acid" is used, the "polyamic acid" may include a polyamic acid that has undergone partial imidization.

Furthermore, the expression "polyimide dissolution rate" refers to the rate observed when a polyimide film formed with an arbitrary thickness, or a polyimide formed with an arbitrary shape, is dissolved using a suitable solution capable of dissolving the polyimide. Examples of suitable solutions include aqueous solutions of inorganic alkali materials such as sodium hydroxide or potassium hydroxide, and aqueous solutions of organic alkali compounds such as tetramethylammonium hydroxide (TMAH) or triethanolamine. Moreover, these solutions may also include a surfactant or an alcohol or the like.

In the present invention, an evaluation of the polyimide dissolution rate is made by measuring the Raman spectral intensity $I(a)$ of imide groups contained within a polyimide (a), and then comparing $I(a)$ with the Raman spectral intensity $I(b)$ of imide groups contained within a polyimide (b) with a known dissolution rate. The polyimide that represents the target of the evaluation and the polyimide with a known dissolution rate are preferably polyimides of the same type, that is, are preferably polyimides having the same repeating units, obtained using the same tetracarboxylic dianhydride and the same diamine. The polyimide that represents the measurement target and the polyimide with a known dissolution rate may also be polyimides of different types.

When a polyimide is dissolved in an alkali solution, the dissolution rate is affected by the quantity of acid groups within the polyimide. The dissolution rate tends to be faster with higher numbers of acid groups, and slower with lower numbers of acid groups. In other words, the dissolution rate tends to be slower with higher numbers of imide groups, and faster with lower numbers of imide groups. Accordingly, in those cases where $I(a)>I(b)$, the dissolution rate for the polyimide (a) can be evaluated to be slower than the dissolution rate for the polyimide (b). In contrast, in those cases where $I(a)<I(b)$, the dissolution rate for the polyimide (a) can be evaluated to be faster than the dissolution rate for the polyimide (b).

Figure 2:
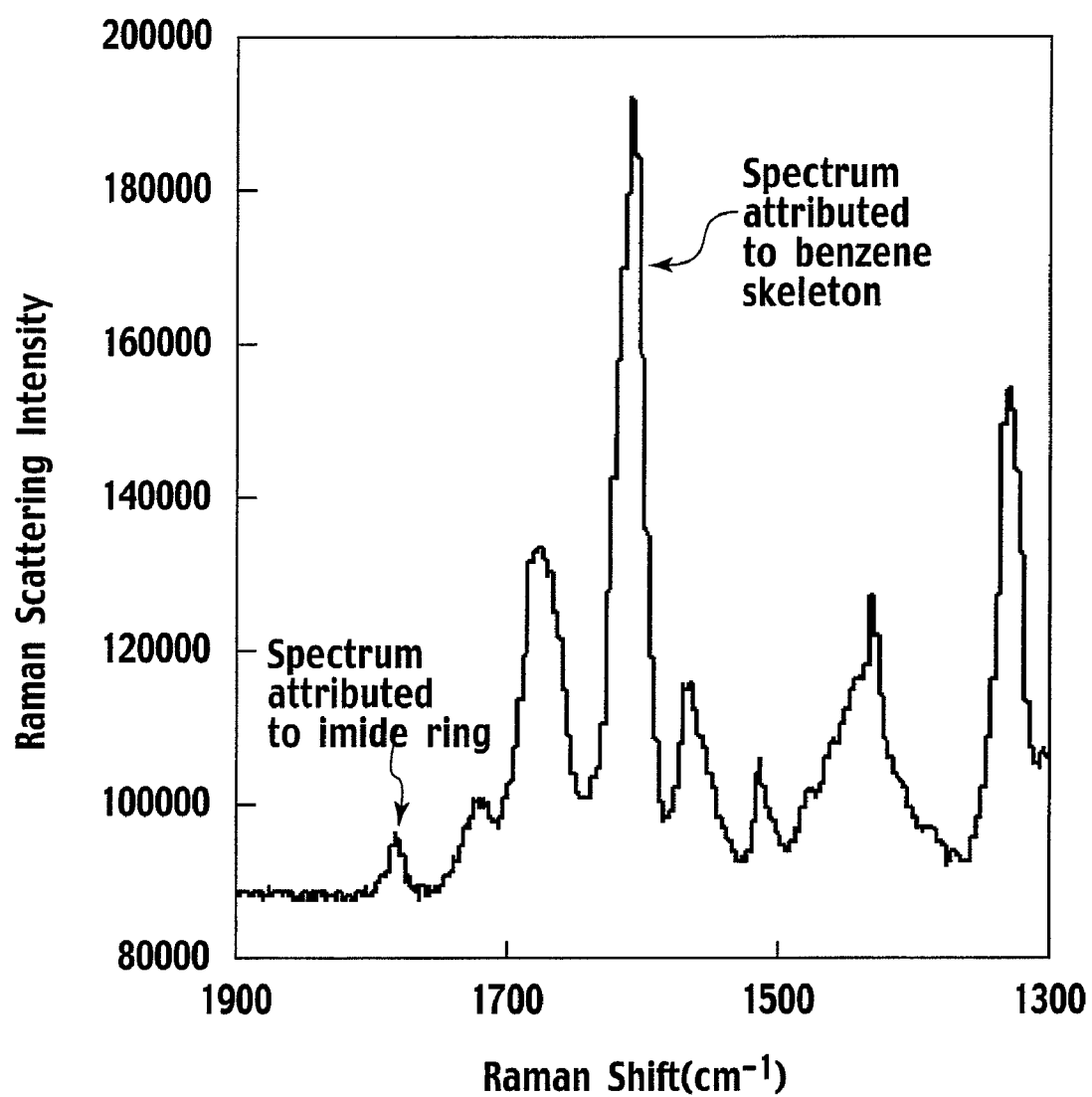
FIG. 2 is a diagram showing an example of a Raman spectrum of a polyimide.
Figure 3:
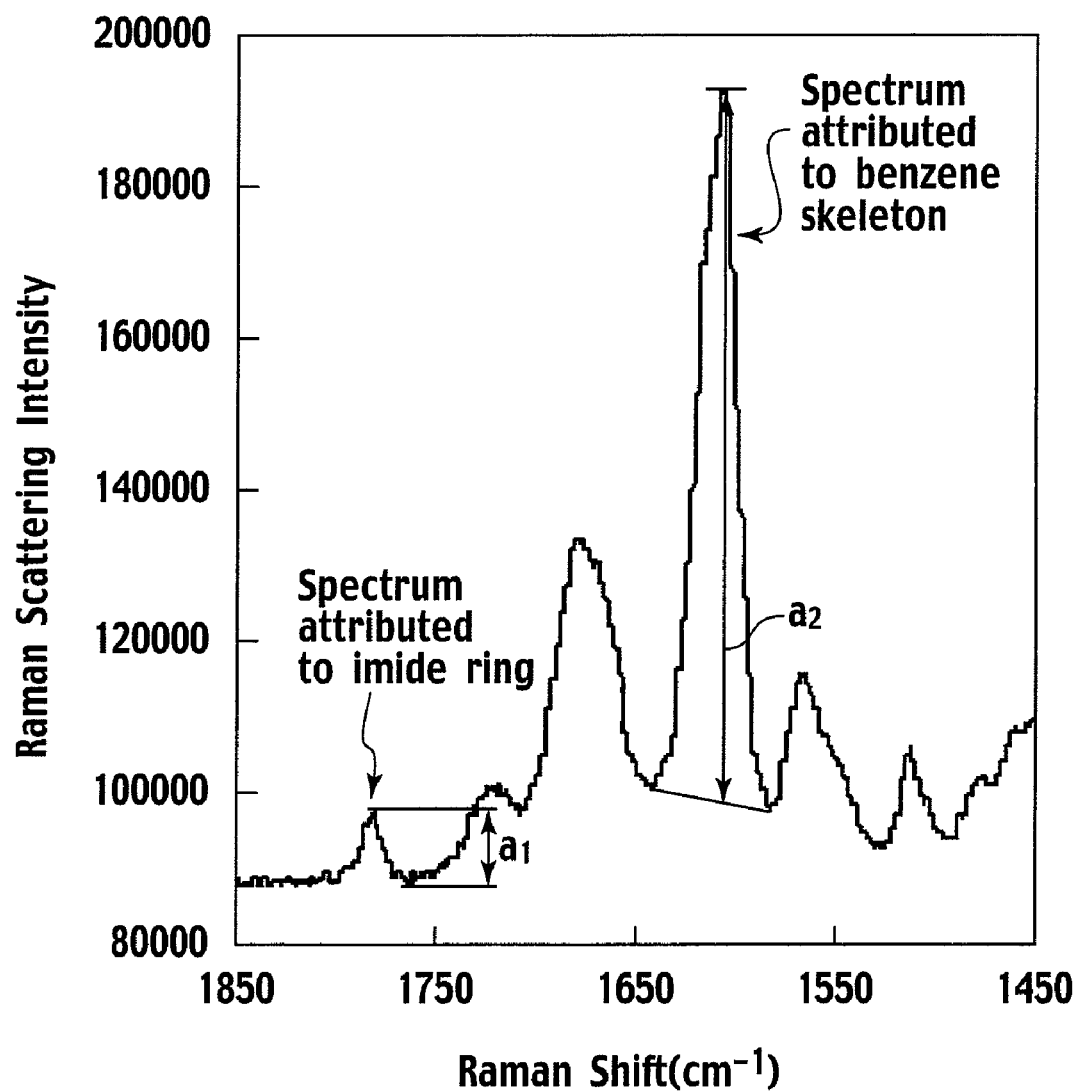
FIG. 3 is a diagram showing an example of a Raman spectrum of a polyimide.

The polyimide that represents the target of the evaluation and the polyimide of known concentration are preferably polyimides obtained using an aromatic tetracarboxylic dianhydride and/or an aromatic diamine. The aromatic rings are preferably benzene rings. In such cases, because the polyimides contain an aromatic ring, the intensity ratio $I(a_1)/I(a_2)$ between the Raman spectral intensity $I(a_1)$ of imide groups and the Raman spectral intensity $I(a_2)$ of aromatic rings contained within the polyimide that represents the target of the evaluation can be compared with the intensity ratio $I(b_1)/I(b_2)$ between the Raman spectral intensity $I(b_1)$ of imide groups and the Raman spectral intensity $I(b_2)$ of aromatic rings contained within the polyimide with a known dissolution rate. For example, in the case where the polyimide dissolution rate is evaluated partway through the process (2), then although the quantity of imide groups contained within the polyimide varies during the process (2), the quantity of aromatic rings does not change. Accordingly, by displaying the level of Raman spectral intensity for the imide groups referenced against the Raman spectral intensity of the aromatic rings, a more accurate evaluation can be made. FIG. 1 shows a Raman spectrum for a polyamic acid measured across a wave number range from 1,300 to 1,900 cm$^{-1}$. FIG. 2 shows a Raman spectrum for a polyimide measured across a wave number range from 1,300 to 1,900 cm$^{-1}$. In FIG. 2, a Raman spectral peak attributed to imide groups appears at a wave number in the vicinity of 1780 cm$^{-1}$. The spectral peak attributed to benzene rings, which appears at a wave number in the vicinity of 1610 cm$^{-1}$, appears in both FIG. 1 and FIG. 2. In the present invention, the peak height can be used as an indication of spectral intensity, and FIG. 3 shows the spectral peak height attributed to imide groups and the spectral peak height attributed to benzene rings.

Instead of the peak height, the peak surface area can also be used as an indication of spectral intensity.

Furthermore, by creating a correlation equation between the intensity ratio $I(b_1)/I(b_2)$ and the dissolution rate for the polyimide of known concentration, and then using this correlation equation as a calibration curve, the dissolution rate of the polyimide that represents the target of the evaluation can be quantified.

In the present invention, the Raman spectrometer apparatus may use any type of apparatus, although the use of a microlaser Raman spectrometer is preferred.

The intensity of the spectrum that appears in the vicinity of wave numbers from 1750 to 1830 cm$^{-1}$ can be measured as the spectrum attributable to imide groups. Furthermore, the intensity of the spectrum that appears in the vicinity of wave numbers from 1570 to 1670 cm$^{-1}$ can be measured as the spectrum attributable to benzene rings.

Next is a description of a method of producing a polyimide according to the present invention. In the present invention, the polyimide is preferably obtained using a method of producing a polyimide that comprises (1) a process of obtaining a polyamic acid using a tetracarboxylic dianhydride and a diamine (also referred to as process (1)), and (2) a process of obtaining a polyimide by heating the polyamic acid (also referred to as process (2)).

The condensation reaction between the tetracarboxylic dianhydride and the diamine is conducted within an organic solvent. During this reaction, the respective quantities of the tetracarboxylic dianhydride and the diamine are preferably set such that the quantity of diamine is within ±10% of being equimolar with the quantity of the tetracarboxylic dianhydride. Furthermore, the order in which each component is added is arbitrary. Examples of the organic solvent used during this synthesis include dimethylacetamide, dimethylformamide, N-methyl-2-pyrrolidone, dimethylsulfoxide, hexamethylphosphorylamide, m-cresol, and o-chlorophenol.

The reaction temperature is preferably within a range from 20° C. to no more than 100° C., and is even more preferably from 30 to 80° C. As the reaction progresses, the viscosity of the reaction solution gradually increases. First, a polyamic acid that acts as a polyimide precursor is produced.

Subsequently, the polyimide can be obtained by subjecting the polyamic acid to a cyclodehydration. The cyclodehydration can be conducted either by a method that involves conducting a heat treatment at 40 to 100° C. for a period of 5 to 40 hours, or by a chemical method. In the case of a method that involves conducting a heat treatment at 40 to 100° C., the reaction is preferably conducted while the water generated by the dehydration reaction undergoes continual removal from the system. In such cases, the water may be removed by azeotropic distillation with benzene, toluene or xylene or the like. The synthesis of the polyamic acid and the cyclodehydration effected by heat treatment need not necessarily be clearly separated processes.

In those cases where the cyclodehydration is conducted by a chemical method, an acid anhydride such as acetic anhydride, propionic anhydride or benzoic anhydride, or a carbodiimide compound such as dicyclohexylcarbodiimide can be added as a cyclization agent. If necessary, a cyclization catalyst such as pyridine, isoquinoline, trimethylamine, aminopyridine or imidazole may also be used. The cyclization agent or cyclization catalyst is preferably used in a quantity equivalent to 1 to 8 mols per 1 mol of the tetracarboxylic dianhydride.

In a method of producing a polyimide according to the present invention, the Raman spectral intensity of imide groups and/or carboxyl groups contained within the polyimide is measured by Raman spectroscopy, and reaction control is then conducted on the basis of the results of that measurement. As described above, the Raman spectral intensity of the imide groups and/or carboxyl groups is preferably determined as an intensity ratio relative to the Raman spectral intensity of benzene rings or the like. Measurement of the Raman spectral intensity can be conducted off-line, on-line or in-line. The measurement is preferably conducted either on-line or in-line. Cases in which measurement is conducted on the polyimide obtained upon completion of the process (2) are included within the production method of the present invention. The term "on-line" refers to a method in which, during the polyimide production process, the polyimide is not sampled for the purpose of measurement, but rather, the Raman spectral intensity is measured continuously, whereas the term "in-line" refers to a method in which, during the polyimide production process, the polyimide is sampled as appropriate for the purpose of measurement, and the Raman spectral intensity of the sample is then measured. On-line measurement of the Raman spectral intensity can be realized, for example, by using a fiber optic probe.

Reaction control includes adjustment of the reaction temperature, adjustment of the reaction time, and addition of the tetracarboxylic dianhydride and/or diamine raw materials. In a production method of the present invention, the Raman spectral intensity of imide groups and/or carboxyl groups is preferably measured during the process (2), and reaction control then conducted on the basis of the result of the measurement.

Figure 8:
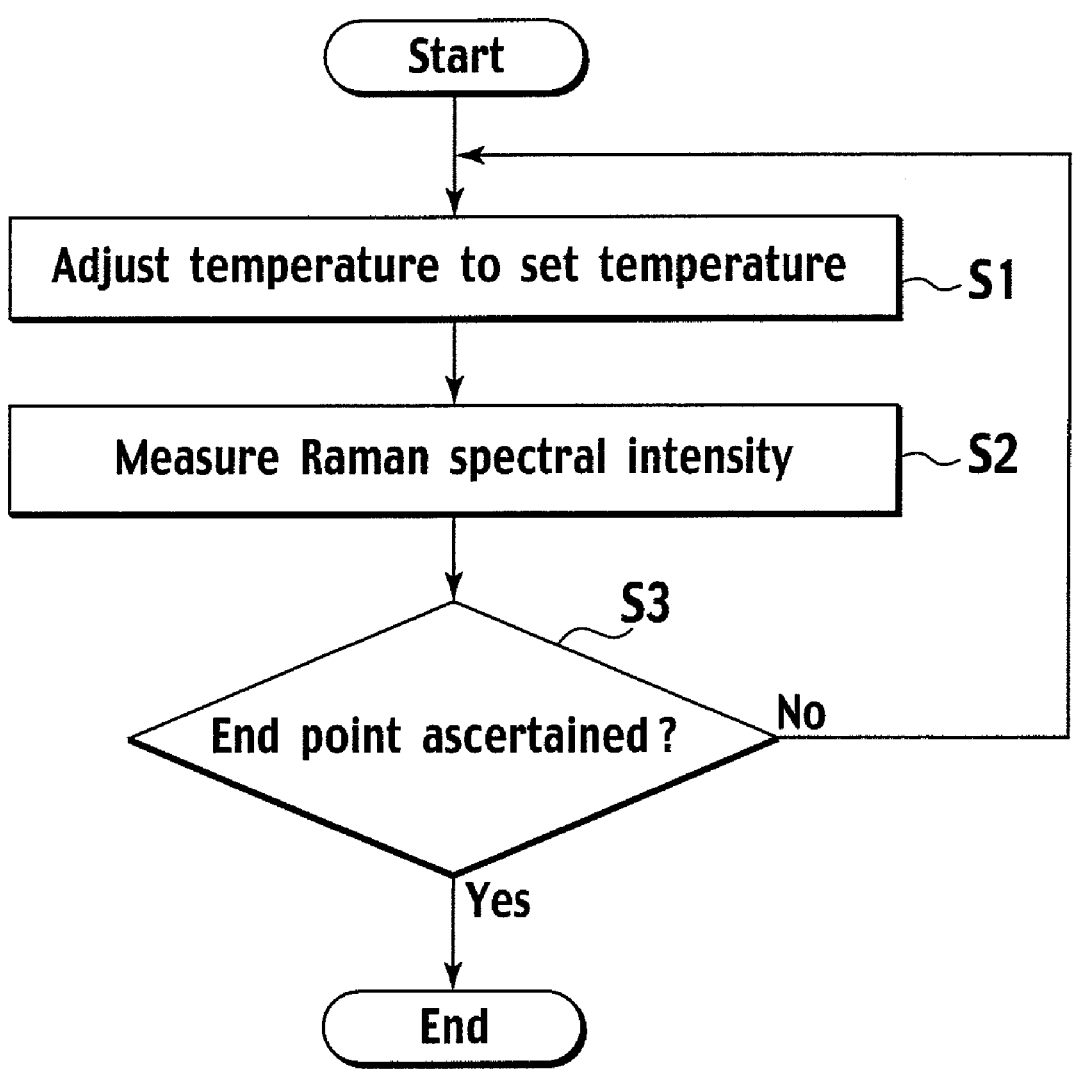
FIG. 8 is a flowchart showing an example of a reaction control sequence in a method of producing a polyimide according to the present invention.

During the process (2), an example in which the Raman spectral intensity of imide groups is measured and the heating temperature and heating time are then adjusted on the basis of the result of the measurement, includes a step (S1) of adjusting the temperature to a set temperature, a step (S2) of measuring the Raman spectral intensity, and a step (S3) of ascertaining the reaction end point. FIG. 8 is a flowchart showing an example of the process (2). First, in S1, the temperature is adjusted to a set temperature. Once a suitable time has elapsed following temperature adjustment, a Raman spectral intensity measurement is conducted in S2, and then a decision as to whether the end point has been reached is made in S3 on the basis of the measurement value. In S3, if a target Raman spectral intensity has been achieved, then a judgment is made to end the process (2). If the target Raman spectral intensity has not been reached, the process (2) continues. The intensity ratio $I(a_1)/I(a_2)$ may also be determined as the Raman spectral intensity.

Moreover, in a method of producing a polyimide according to the present invention, reaction control can also be conducted on the basis of a combination of the result of the Raman spectral intensity measurement, and the result of measuring another arbitrary property such as the viscosity or molecular weight of the polyamic acid or the polyimide. In the production method of the present invention, it is preferable that during the process (2), the Raman spectral intensity of imide groups and/or carboxyl groups is measured, and the viscosity of the polyimide is also measured, and reaction control is then conducted on the basis of the results of these measurements.

Figure 9:
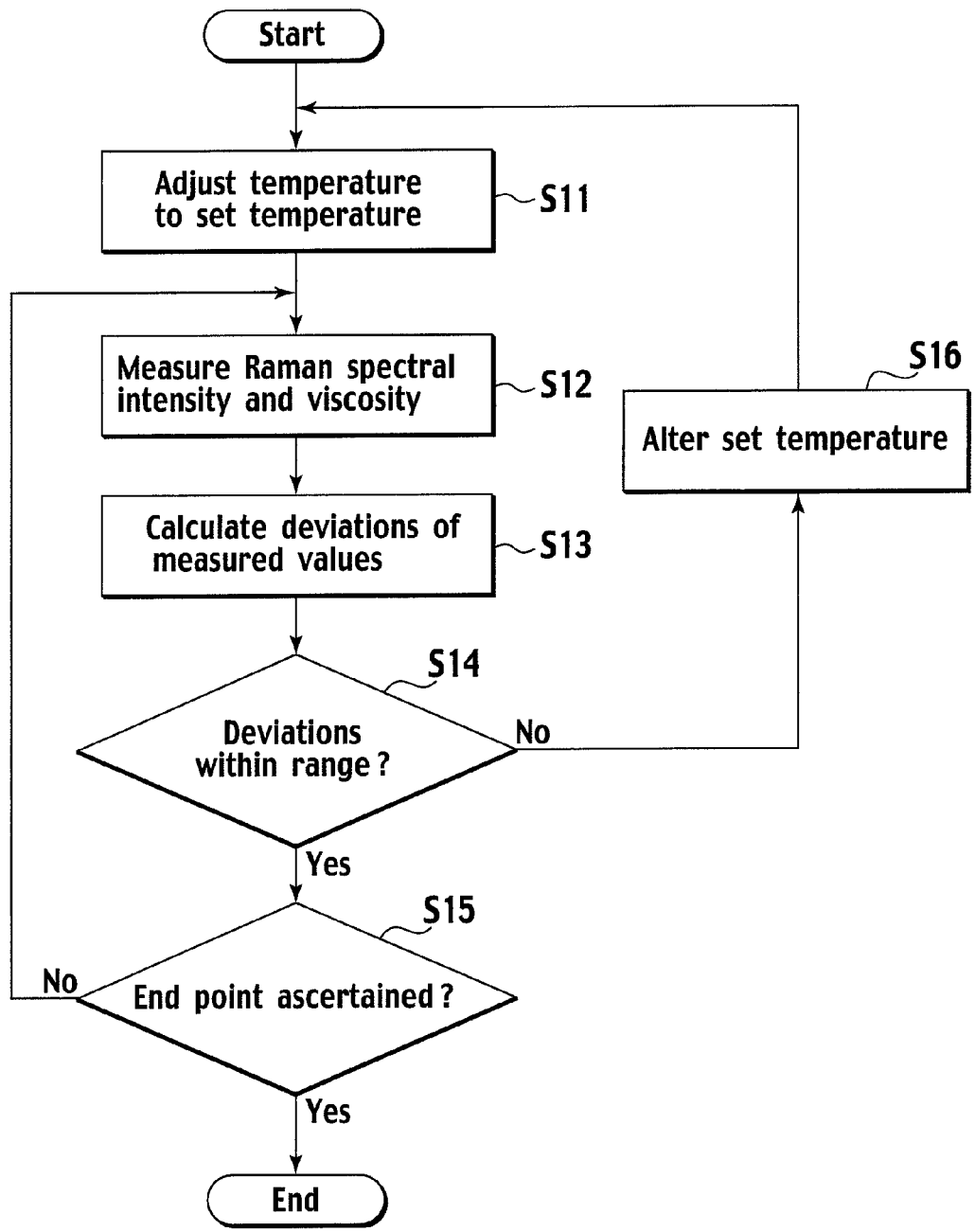
FIG. 9 is a flowchart showing an example of a reaction control sequence in a method of producing a polyimide according to the present invention.

During the process (2), an example in which the Raman spectral intensity of imide groups and the polyimide viscosity are measured, and the heating temperature and heating time are then adjusted on the basis of the results of these measurements, includes a step (S11) of adjusting the temperature to a set temperature, a step (S12) of measuring the Raman spectral intensity and the viscosity, a step (S13) of calculating the deviations in the measured values, a step (S14) of checking the deviations, a step (S15) of ascertaining the reaction end point, and where necessary, a step (S16) of altering the set temperature. FIG. 9 is a flowchart showing an example of the process (2). First, in S11, the temperature is adjusted to a set temperature. Once a suitable time has elapsed following temperature adjustment, the Raman spectral intensity and viscosity of the polyimide is measured in S12.

Figure 4:
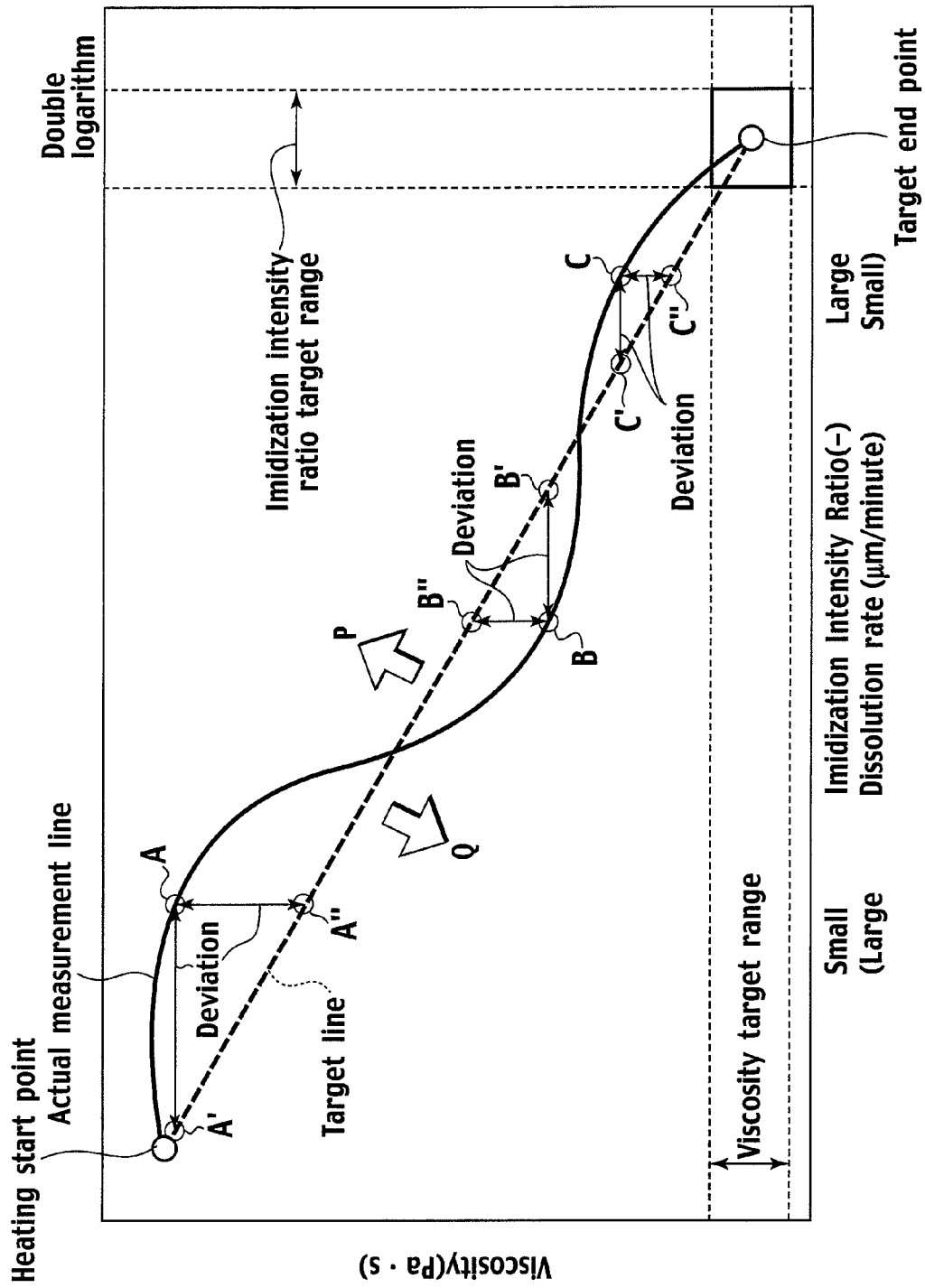
FIG. 4 is a diagram showing a target line for the Raman spectral intensity of imide groups (the polyimide dissolution rate) and the viscosity.

Based on the resulting measured values, the deviations (displacements) in the measured values are calculated in S13. As shown in FIG. 4, the actual calculation of the deviations in the measured values is conducted using a target line that represents the ideal relationship between Raman spectral intensity (the polyimide dissolution rate) and the viscosity. In FIG. 4, the target line for the Raman spectral intensity and the viscosity, between a start point (the point where temperature was adjusted to the set temperature) and an end point (the point where the reaction has finished), is represented by a dotted line. In the process (2), heating tends to increase the quantity of imide groups and decrease the viscosity. In S13, the deviations between the target line and the measured values are determined. First, the measured values for the Raman spectral intensity and the viscosity are plotted onto FIG. 4 (such as the point A $(x_1, y_1)$ in FIG. 4). Both the Raman spectral intensity deviation and the viscosity deviation are determined. First is a description of the determination of the Raman spectral intensity deviation. First, the point A'$(x_2, y_2)$ on the target line that has the same y value (viscosity value) as the point A $(x_1, y_1)$ is determined. The Raman spectral intensity deviation at the point A can then be calculated from the formula: $[(x_1-x_2)/(x_2)]\times100(\%)$. Next is a description of the determination of the viscosity deviation. First, the point A" $(x_3, y_3)$ on the target line that has the same x value (Raman spectral intensity value) as the point A $(x_1, y_1)$ is determined. The viscosity deviation at the point A can then be calculated from the formula: $[(y_1-y_3)/(y_3)]\times100(\%)$. The same calculations can be performed at the points B and C. For example, in a case where, for a certain Raman spectral intensity value, the viscosity target line value is 60 Pa·s and the measured value is 63 Pa·s, the viscosity deviation can be determined from the formula: $[(63-60)/60]\times100=5(\%)$. In an additional example, if the viscosity target line value is 10 Pa·s and the measured value is 8 Pa·s for a certain Raman spectral intensity value, then the viscosity deviation can be determined from the formula $[(8-10)/8]\times100=-25(\%)$.

Subsequently, the deviations are checked in S14. In this step, a judgment is made as to whether or not the deviations calculated at S13 fall within target deviations. If the deviations fall within these target deviations, then the processing proceeds to S15. If the deviations fall outside these target deviations, then the processing proceeds to S16. These target deviations can be determined from the Raman spectral intensity target range and viscosity target range for the polyimide that represents the final target. For example, if the aim is to obtain a polyimide with a Raman spectral intensity from $X_1$ to $X_2$ (wherein, $X_1<X_2$), then the Raman spectral intensity target deviation can be determined using the formula: $\pm[(X_2-X_1)/\{(X_2+X_1)/2\}]/2\times100(\%)$. Similarly, if the aim is to obtain a polyimide with a viscosity from $Y_1$ to $Y_2$ (Pa·s) (wherein, $Y_1<Y_2$), then the viscosity target deviation can be determined using the formula: $\pm[(Y_2-Y_1)/\{(Y_2+Y_1)/2\}]/2\times100(\%)$.

In this description, the deviations were determined using the formulas outlined above, but the present invention is not limited to this case, and any method can be used for determining the deviations, provided the displacements from the target line can be determined. Furthermore, from the viewpoint of precision, the measurement of the deviations (S13) and the checking of those deviations (S14) are preferably performed for both the Raman spectral intensity and the viscosity, but the target polyimide can also be obtained by performing the steps (S13) and (S14) for only one of these properties.

Subsequently, a decision as to whether the end point has been reached is made in S15. If the measured values are within the Raman spectral intensity target range and the viscosity target range for the polyimide then the reaction is ended. If the measured values do not satisfy the Raman spectral intensity target range or the viscosity target range, then the reaction is continued.

In S14, if the deviations do not satisfy the target deviations, then the set temperature is altered. Alteration of the set temperature is conducted by ascertaining the changes in the imidization reaction rate and the viscosity reduction reaction rate when the temperature is either raised or lowered from the initial set temperature. With due consideration of which is the larger and which is the smaller of the Raman spectral intensity deviation and the viscosity deviation, and which is the larger and which is the smaller of the imidization reaction rate and the viscosity reduction reaction rate that accompany alterations in the set temperature, the set temperature is altered to a temperature that is predicted to move the measured values closer to the target line.

For example, in those cases where, upon comparison with the Raman spectral intensity and viscosity target line, either the measured values have a large viscosity value at a certain Raman spectral intensity value or a large Raman spectral intensity value at a certain viscosity value (the region indicated by P in the graph of FIG. 4), an adjustment can be made to increase the heating temperature. Furthermore, in those cases where, upon comparison with the imide group Raman spectral intensity and viscosity target line, either the measured values have a small viscosity value at a certain Raman spectral intensity value or a small Raman spectral intensity value at a certain viscosity value (the region indicated by Q in the graph of FIG. 4), an adjustment can be made to reduce the heating temperature. Furthermore, in another example, in those cases where, upon comparison with the Raman spectral intensity and viscosity target line, either the measured values have a large viscosity value at a certain Raman spectral intensity value or a large Raman spectral intensity value at a certain viscosity value (the region indicated by P in the graph of FIG.

4), an adjustment can be made to reduce the heating temperature. Furthermore, in those cases where, upon comparison with the imide group Raman spectral intensity and viscosity target line, either the measured values have a small viscosity value at a certain Raman spectral intensity value or a small Raman spectral intensity value at a certain viscosity value (the region indicated by Q in the graph of FIG. 4), an adjustment can be made to increase the heating temperature.

In a production method of the present invention, the above types of reaction control can also be automated by using a computer equipped with a program capable of performing reaction control. For example, the measurements of the Raman spectral intensity and viscosity can be conducted automatically, the results of these measurements and the type of Raman spectral intensity and viscosity target line shown in FIG. 4 then used to automatically calculate the optimal heating temperature and heating time required to obtain the target polyimide, and the results of these calculations then used to automatically adjust the actual heating temperature and heating time during the reaction.

In this manner, by using a production method of the present invention, an automated polyimide production apparatus (automated production line) comprising a polyimide production device, a Raman spectral intensity measuring device, a viscosity measuring device, and a reaction control mechanism such as a computer can be provided.

Furthermore, in an alternative method of producing a polyimide according to the present invention, a dissolution rate evaluation is conducted using the above method of evaluating the dissolution rate, and reaction control is then conducted on the basis of the result of that dissolution rate evaluation.

For example, an evaluation of the dissolution rate can be conducted during the process (2), and the heating temperature and/or heating time of the process (2) then controlled on the basis of the results of that dissolution rate evaluation. An example of the production of a polyimide with a desired dissolution rate within an alkali solution is outlined below. The polyimide dissolution rate can be determined from the Raman spectral intensity and a calibration curve produced using a polyimide of known concentration. In the flowchart of FIG. 8, the Raman spectral intensity is measured in S2 and an evaluation of the dissolution rate is made from the measured intensity value, and reaction control can then be conducted in S3 by making a judgment on the basis of the dissolution rate. Furthermore, in the flowchart of FIG. 9, the Raman spectral intensity is measured in S12 and an evaluation of the dissolution rate is made from the measured intensity value, a dissolution rate deviation is determined in S13, a judgment is made in S14 or S15 on the basis of the dissolution rate instead of the Raman spectral intensity, and reaction control can then be conducted in S16 by altering the set temperature on the basis of the deviation in the dissolution rate instead of the deviation in the Raman spectral intensity.

There are no particular restrictions on the diamine used in a production method of the present invention, and suitable examples include aliphatic diamines such as 1,2-diaminoethane, 1,3-diaminopropane, 1,4-diaminobutane and 1,5-diaminopentane, aromatic diamines such as o-phenylenediamine, m-phenylenediamine, p-phenylenediamine, 3,3'-diaminodiphenyl ether, 3,4'-diaminodiphenyl ether, 4,4'-diaminodiphenyl ether, 3,3'-diaminodiphenylmethane, 3,4'-diaminodiphenylmethane, 4,4'-diaminodiphenylmethane, 3,3'-diaminodiphenyldifluoromethane, 3,4'-diaminodiphenyldifluoromethane, 4,4'-diaminodiphenyldifluoromethane, 3,3'-diaminodiphenyl sulfone, 3,4'-diaminodiphenyl sulfone, 4,4'-diaminodiphenyl sulfone, 3,3'-diaminodiphenyl sulfide, 3,4'-diaminodiphenyl sulfide, 4,4'-diaminodiphenyl sulfide, 3,3'-diaminodiphenyl ketone, 3,4'-diaminodiphenyl ketone, 4,4'-diaminodiphenyl ketone, 2,2-bis(3-aminophenyl)propane, 2,2'-(3,4'-diaminodiphenyl)propane, 2,2-bis(4-aminophenyl)propane, 2,2-bis(3-aminophenyl)hexafluoropropane, 2,2-(3,4'-diaminodiphenyl)hexafluoropropane, 2,2-bis(4-aminophenyl)hexafluoropropane, 1,3-bis(3-aminophenoxy)benzene, 1,4-bis(3-aminophenoxy)benzene, 1,4-bis(4-aminophenoxy)benzene, 3,3'-(1,4-phenylenebis(1-methylethylidene))bisaniline, 3,4'-(1,4-phenylenebis(1-methylethylidene))bisaniline, 4,4'-(1,4-phenylenebis(1-methylethylidene))bisaniline, 2,2-bis(4-(3-aminophenoxy)phenyl) propane, 2,2-bis(4-(4-aminophenoxy)phenyl)propane, 2,2-bis(4-(3-aminophenoxy)phenyl)hexafluoropropane, 2,2-bis(4-(4-aminophenoxy)phenyl)hexafluoropropane, bis(4-(3-aminophenoxy)phenyl)sulfide, bis(4-(4-aminophenoxy)phenyl) sulfide, bis(4-(3-aminophenoxy)phenyl) sulfone, and bis(4-(4-aminophenoxy)phenyl) sulfone, as well as 1,1,3,3-tetramethyl-1,3-bis(4-aminophenyl)disiloxane, 1,1,3,3-tetraphenoxy-1,3-bis(4-aminoethyl)disiloxane, 1,1,3,3-tetraphenyl-1,3-bis(2-aminoethyl)disiloxane, 1,1,3,3-tetraphenyl-1,3-bis(3-aminopropyl)disiloxane, 1,1,3,3-tetramethyl-1,3-bis(2-aminoethyl)disiloxane, 1,1,3,3-tetramethyl-1,3-bis(3-aminopropyl)disiloxane, 1,1,3,3-tetramethyl-1,3-bis(3-aminobutyl)disiloxane, 1,3-dimethyl-1,3-dimethoxy-1,3-bis(4-aminobutyl)disiloxane, 1,1,3,3,5,5-hexamethyl-1,5-bis(4-aminophenyl)trisiloxane, 1,1,5,5-tetraphenyl-3,3-dimethyl-1,5-bis(3-aminopropyl) trisiloxane, 1,1,5,5-tetraphenyl-3,3-dimethoxy-1,5-bis(4-aminobutyl)trisiloxane, 1,1,5,5-tetraphenyl-3,3-dimethoxy-1,5-bis(5-aminopentyl)trisiloxane, 1,1,5,5-tetramethyl-3,3-dimethoxy-1,5-bis(2-aminoethyl)trisiloxane, 1,1,5,5-tetramethyl-3,3-dimethoxy-1,5-bis(4-aminobutyl) trisiloxane, 1,1,5,5-tetramethyl-3,3-dimethoxy-1,5-bis(5-aminopentyl)trisiloxane, 1,1,3,3,5,5-hexamethyl-1,5-bis(3-aminopropyl)trisiloxane, 1,1,3,3,5,5-hexaethyl-1,5-bis(3-aminopropyl)trisiloxane, and 1,1,3,3,5,5-hexapropyl-1,5-bis(3-aminopropyl)trisiloxane. These compounds may be used either alone, or in combinations of two or more different compounds. In the present invention, the use of an aromatic diamine is preferred.

There are no particular restrictions on the tetracarboxylic dianhydride, and suitable examples include pyromellitic dianhydride, 3,3',4,4'-diphenyltetracarboxylic dianhydride, 2,2',3,3'-diphenyltetracarboxylic dianhydride, 2,2-bis(3,4-dicarboxyphenyl)propane dianhydride, 2,2-bis(2,3-dicarboxyphenyl)propane dianhydride, 1,1-bis(2,3-dicarboxyphenyl)ethane dianhydride, 1,1-bis(3,4-dicarboxyphenyl)ethane dianhydride, bis(2,3-dicarboxyphenyl)methane dianhydride, bis(3,4-dicarboxyphenyl)methane dianhydride, bis(3,4-dicarboxyphenyl) sulfone dianhydride, 3,4,9,10-perylenetetracarboxylic dianhydride, bis(3,4-dicarboxyphenyl)ether dianhydride, benzene-1,2,3,4-tetracarboxylic dianhydride, 3,3',4,4'-benzophenonetetracarboxylic dianhydride, 2,2',3,3'-benzophenonetetracarboxylic dianhydride, 2,3,3',4'-benzophenonetetracarboxylic dianhydride, 1,2,5,6-naphthalenetetracarboxylic dianhydride, 2,3,6,7-naphthalenetetracarboxylic dianhydride, 1,2,4,5-naphthalenetetracarboxylic dianhydride, 1,4,5,8-naphthalenetetracarboxylic dianhydride, 2,6-dichloronaphthalene-1,4,5,8-tetracarboxylic dianhydride, 2,7-dichloronaphthalene-1,4,5,8-tetracarboxylic dianhydride, 2,3,6,7-tetrachloronaphthalene-1,4,5,8-tetracarboxylic dianhydride, phenanthrene-1,8,9,10-tetracarboxylic dianhydride, pyrazine-2,3,5,6-tetracarboxylic dianhydride, thiophene-2,3,4,5-tetracarboxylic dianhydride, 2,3,3',4'-biphenyltetracarboxylic dianhydride, 3,3',4,4'-biphenyltetracarboxylic dianhydride, 2,2',3,3'-biphenyltetracarboxylic dianhydride, bis(3,4- dicarboxyphenyl)dimethylsilane dianhydride, bis(3,4-dicarboxyphenyl)methylphenylsilane dianhydride, bis(3,4-dicarboxyphenyl)diphenylsilane dianhydride, 1,4-bis(3,4-dicarboxyphenyldimethylsilyl)benzene dianhydride, 1,3-bis(3,4-dicarboxyphenyl)-1,1,3,3-tetramethyldicyclohexane dianhydride, ethylenetetracarboxylic dianhydride, 1,2,3,4-butanetetracarboxylic dianhydride, decahydronaphthalene-1,4,5,8-tetracarboxylic dianhydride, 4,8-dimethyl-1,2,3,5,6,7-hexahydronaphthalene-1,2,5,6-tetracarboxylic dianhydride, cyclopentane-1,2,3,4-tetracarboxylic dianhydride, pyrrolidine-2,3,4,5-tetracarboxylic dianhydride, 1,2,3,4-cyclobutanetetracarboxylic dianhydride, bicyclo-[2,2,2]-oct-7-ene-2,3,5,6-tetracarboxylic dianhydride, 2,2-bis(3,4-dicarboxyphenyl)hexafluoropropane dianhydride, 2,2-bis[4-(3,4-dicarboxyphenoxy)phenyl]hexafluoropropane dianhydride, 4,4'-bis(3,4-dicarboxyphenoxy)diphenyl sulfide dianhydride, 4,4'-(4,4'-isopropylidenediphenoxy)diphthalic dianhydride, tetrahydrofuran-2,3,4,5-tetracarboxylic dianhydride, and bis(exo-bicyclo[2,2,1]heptane-2,3-dicarboxylic dianhydride) sulfone. These compounds may be used either alone, or in combinations of two or more different compounds. In the present invention, the use of an aromatic tetracarboxylic dianhydride is preferred.

In the present invention, the use of polyimides obtained using 4,4'-diaminodiphenyl ether as the diamine and pyromellitic dianhydride as the tetracarboxylic dianhydride, and polyimides obtained using 4,4'-diaminodiphenyl ether as the diamine and 3,3'4,4'-benzophenonetetracarboxylic dianhydride as the tetracarboxylic dianhydride is particularly preferred.

The weight average molecular weight of the polyimide is preferably within a range from 20,000 to 150,000, even more preferably from 30,000 to 100,000, and is most preferably from 50,000 to 80,000. If the molecular weight is less than 20,000, then the film characteristics of the polyimide may deteriorate. If the molecular weight exceeds 150,000, then film formation may become difficult. The weight average molecular weight of the polyimide refers to a value measured using gel permeation chromatography and referenced against standard polystyrenes.

The viscosity of the polyimide is preferably within a range from 0.1 to 1,500 Pa·s, even more preferably from 1 to 1,000 Pa·s, and is most preferably from 10 to 500 Pa·s. The polyimide viscosity can be measured using an E-type viscometer.

According to a method of evaluating dissolution rate according to the present invention, the evaluation of the polyimide dissolution rate is simplified, and the time required for the evaluation can be shortened. Furthermore, the dissolution rate can be quantified by using a calibration curve. Moreover, in a method of producing a polyimide, the results of the dissolution rate evaluation, which are obtained in real-time, can be used for conducting control of conditions such as the reaction temperature, enabling a polyimide of uniform quality to be obtained with ease.

In the above description, the method of evaluating the polyimide dissolution rate and method of producing a polyimide that use Raman spectroscopy were described using examples in which the Raman spectral intensity of the imide groups within the polyimide was measured, but instead of measuring the Raman spectral intensity of the imide groups within the polyimide, the Raman spectral intensity of the carboxyl groups within the polyimide can also be measured. In addition, in order to improve the reliability of the evaluation, the Raman spectral intensities of both the imide groups and the carboxyl groups may be measured. A polyimide obtained using the present invention can be used favorably as a surface protective film or interlayer insulation film or the like for a semiconductor element during the production of a semiconductor device by conventional methods.

According to a method of evaluating dissolution rate of the present invention, the dissolution rate of a polyimide can be evaluated simply and quickly. Furthermore, according to a method of producing a polyimide of the present invention, a target polyimide can be obtained simply and efficiently. Moreover, by incorporating a method of evaluating dissolution rate according to the present invention, preferably in combination with a viscosity measurement, as an on-line or in-line test within a polyimide production (synthesis) line, and then using this method to conduct reaction control of the production process, a polyimide of uniform quality can be obtained in a stable manner.

Furthermore, according to a method of evaluating dissolution rate and a method of producing a polyimide according to the present invention, the measurement of the Raman spectral intensity of imide groups and the measurement of the viscosity can be conducted either on-line or in-line. For example, during the process (2), by using a fiber optic probe, the Raman spectral intensity of the polyimide can be measured continuously throughout the reaction without sampling, and furthermore, by fitting an oscillating viscometer within the reaction vessel, the polyimide viscosity can also be measured continuously throughout the reaction without sampling. These measurement results can then be sent to a reaction control mechanism, and this reaction control mechanism then used to automatically adjust the heating temperature and heating time. Furthermore, the polyimide may also be sampled as many times as is necessary during the process (2), the Raman spectral intensity of the imide groups and the polyimide viscosity measured for each sample, and the heating temperature and heating time then adjusted on the basis of these measurement results. In a conventional method of measuring the dissolution rate, measuring the dissolution rate partway through the process (2) is problematic, and the dissolution rate measurement is typically conducted on the final polyimide obtained upon completion of the process (2). As a result, in those cases where a polyimide with the targeted dissolution rate could not be obtained, that particular polyimide can not be used in the production of a semiconductor device. Furthermore, in order to cope with the smaller and more complex semiconductor devices of recent years, stringent standards have been set for a wide variety of polyimides, and not only is setting the reaction conditions required to obtain the desired target polyimide very difficult, but even if those settings are made, obtaining the target polyimide in good yield has still proven impossible. However, by employing a method of evaluating the dissolution rate and a method of producing a polyimide according to the present invention, the target polyimide can be produced easily and in high yields by controlling the reaction during the polyimide production process.

EXAMPLES

Example 1

Creation of a Calibration Curve

A 1 L four-neck flask fitted with a stirrer, a thermometer, a nitrogen gas inlet and a calcium chloride tube was charged with 850 g of N-methyl-2-pyrrolidone (NMP), 71.89 g (0.36 mol) of 4,4'-diaminodiphenyl ether (4,4'-DPE) was added and dissolved, and then 78.21 g (0.36 mol) of pyromellitic dianhydride (PMDA) was added, yielding a reaction solution.

This reaction solution was stirred for 3 hours at room temperature, yielding a polyamic acid solution.

The temperature of the thus obtained polyamic acid solution was raised to 80° C. using a hot water bath, and when the temperature of the polyamic acid solution reached 80° C., 6 g of ion-exchanged water was added. Subsequently, the polyamic acid solution was reacted for 12 hours at 80° C., thus yielding a polyimide solution. The weight average molecular weight of the polyimide was 70,000.

The polyimide solution was measured for etching rate, imidization intensity ratio and viscosity, in accordance with the methods described below, at points 1.5 hours (first repetition), 4.5 hours (second repetition), 8 hours (third repetition), and 12 hours (fourth repetition) after the point at which the ion-exchanged water was added to the polyamic acid solution.

<Measurement of Etching Rate (Dissolution Rate)>

Using a spin coater (rate of revolution: 5,000 rpm), the polyamic acid solution was applied to the surface of a 12-inch Si wafer. Subsequently, the polyamic acid on the Si wafer was cured using a curing temperature of 145° C. and a curing time of 30 minutes, thus forming a polyimide film. Using a cutter knife, a section of the polyimide film of dimensions 2×10 mm was cut and removed from the center of the polyimide film-bearing Si wafer, thus yielding a Si wafer for etching rate measurement. When the film thickness was measured at the section where the polyimide film had been removed, the cured film thickness was 4 μm (the initial film thickness). Subsequently, the Si wafer was immersed for 60 seconds in a 2.38% TMAH solution (a positive resist developer, manufactured by Tama Chemicals Co., Ltd.), thereby etching (dissolving) the polyimide film. Following etching, the Si wafer was washed under a stream of water for 100 seconds, and then blown dry with $N_2$. When the film thickness was re-measured at the section where the polyimide film had been removed, in the same manner as that used prior to etching, the film thickness values (film thickness following etching) were first repetition: 3.479 μm, second repetition: 3.535 μm, third repetition: 3.627 μm, and fourth repetition: 3.717 μm respectively. The etching rate (μm/minute) was determined using the formula: [(initial film thickness−film thickness following etching)/etching time]. The film thickness values were measured using a stylus film thickness measuring device (Dektak 3030, manufactured by Ulvac, Inc.).

<Measurement of Imidization Intensity Ratio>

Raman spectroscopic measurements were conducted using a STR series laser Raman spectroscopy system manufactured by Seki Technotron Corporation (imaging spectrometer: STR-250-2, light source: Ar laser (model STR-250-2), rated output: 40 mW, wavelength: 514.5 nm). The imidization intensity ratio was determined from the intensity ratio $I(a_1)/I(a_2)$ between the Raman spectral intensity $I(a_1)$ of imide groups and the Raman spectral intensity $I(a_2)$ of aromatic rings.

<Measurement of Viscosity>

Measurement of the viscosity was conducted using an E-type viscometer (TVE-22, manufactured by Toki Sangyo Co., Ltd.).

Figure 5:
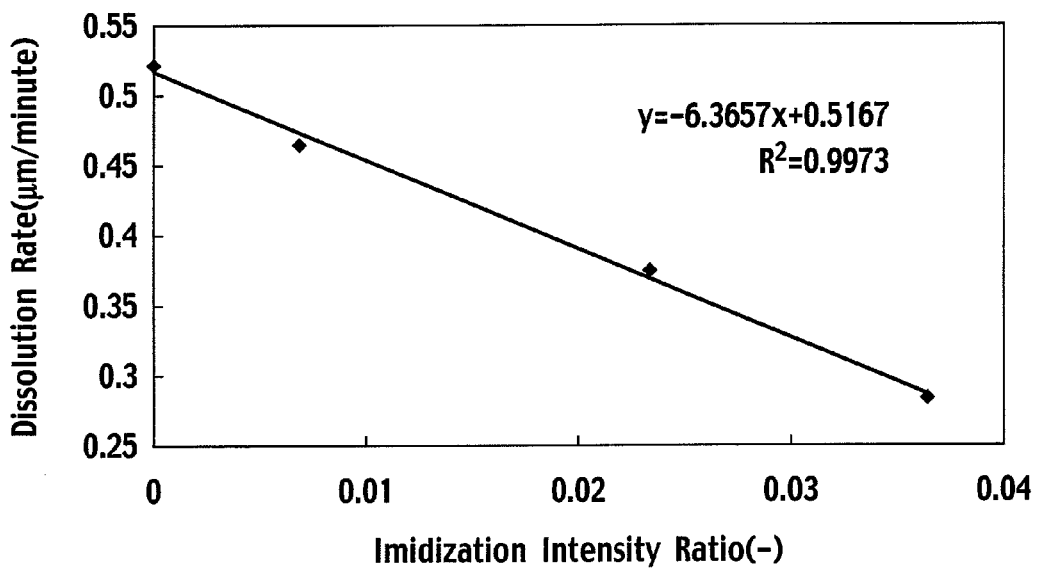
FIG. 5 is a diagram showing a correlation chart (a correlation equation and a calibration curve) for a ratio $I(a_1)/I(a_2)$ between the spectral intensity $I(a_1)$ attributed to imide rings and the spectral intensity $I(a_2)$ attributed to aromatic rings within a polyimide obtained in an example 1, and the dissolution rate.

The polyimide measurement results for the first through fourth repetitions are shown in Table 1. Furthermore, a calibration curve obtained by plotting the imidization intensity ratio along the horizontal axis and the etching rate along the vertical axis is shown in FIG. 5.

TABLE 1

| Sample repetition number (repetition) | Cooking time (hours) | Viscosity (Pa · s) | Imidization intensity ratio (-) | Etching rate (μm/minute) |
|---|---|---|---|---|
| First repetition | 1.5 | 11.3 | 0 | 0.521 |
| Second repetition | 4.5 | 10.2 | 0.00696 | 0.465 |
| Third repetition | 8 | 8.5 | 0.02330 | 0.373 |
| Fourth repetition | 12 | 7.7 | 0.03640 | 0.283 |

[Measurement of Polyimide Dissolution Rate]

A 1 L four-neck flask fitted with a stirrer, a thermometer, a nitrogen gas inlet and a calcium chloride tube was charged with 850 g of N-methyl-2-pyrrolidone (NMP), 71.89 g (0.36 mols) of 4,4'-diaminodiphenyl ether (4,4'-DPE) was added and dissolved, and then 78.21 g (0.36 mols) of pyromellitic dianhydride (PMDA) was added, yielding a reaction solution. This reaction solution was stirred for 3 hours at room temperature, yielding a polyamic acid solution.

The temperature of the thus obtained polyamic acid solution was raised to 80° C. using a hot water bath, and when the temperature of the polyamic acid solution reached 80° C., 6 g of ion-exchanged water was added. Subsequently, the polyamic acid solution was reacted for 12 hours at 80° C., thus yielding a polyimide solution. The weight average molecular weight of the polyimide was 65,000.

Measurement of the imidization intensity ratio for the thus obtained polyimide revealed a result of 0.0124. Based on this imidization intensity ratio and the calibration curve obtained above, the polyimide dissolution rate was evaluated at 0.44 (μm/minute).

Example 2

Creation of a Calibration Curve

A 1 L four-neck flask fitted with a stirrer, a thermometer, a nitrogen gas inlet and a calcium chloride tube was charged with 850 g of N-methyl-2-pyrrolidone (NMP), 57.49 g (0.29 mols) of 4,4'-diaminodiphenyl ether (4,4'-DPE) was added and dissolved, and then 92.51 g (0.29 mols) of 3,3',4,4'-benzophenonetetracarboxylic dianhydride (BTDA) was added, yielding a reaction solution. This reaction solution was stirred for 3 hours at room temperature, yielding a polyamic acid solution.

The temperature of the thus obtained polyamic acid solution was raised to 80° C. using a hot water bath, and when the temperature of the polyamic acid solution reached 80° C., 6 g of ion-exchanged water was added. Subsequently, the polyamic acid solution was reacted for 12 hours at 80° C., thus yielding a polyimide solution. The weight average molecular weight of the polyimide was 80,000.

The polyimide solution was measured for etching rate, imidization intensity ratio and viscosity at points 1.5 hours (first repetition), 4.5 hours (second repetition), 8 hours (third repetition), and 12 hours (fourth repetition) after the point at which the ion-exchanged water was added to the polyamic acid solution. The measurement methods used were the same as those described for the example 1.

Figure 6:
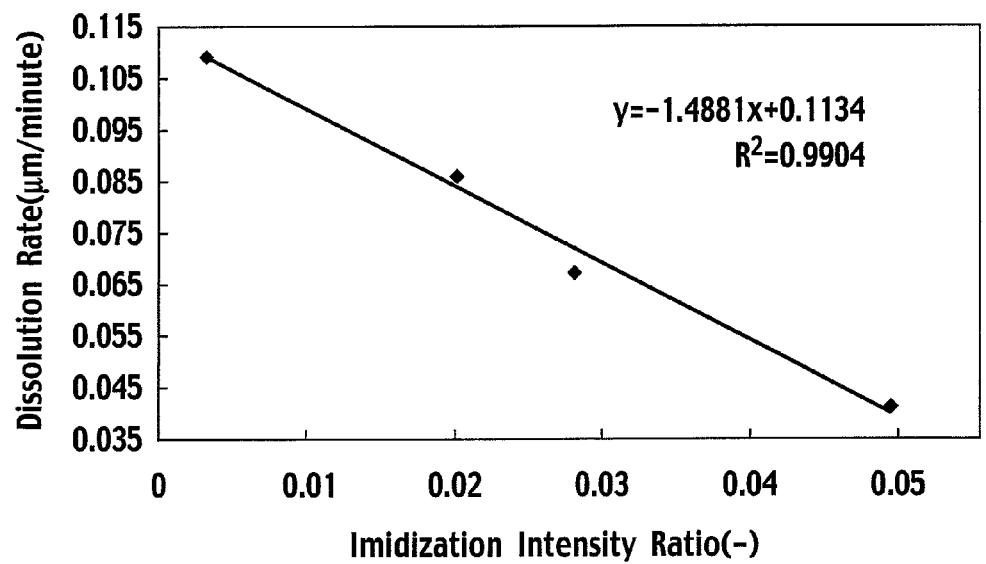
FIG. 6 is a diagram showing a correlation chart (a correlation equation and a calibration curve) for a ratio $I(a_1)/I(a_2)$ between the spectral intensity $I(a_1)$ attributed to imide rings and the spectral intensity $I(a_2)$ attributed to aromatic rings within a polyimide obtained in an example 2, and the dissolution rate.

The polyimide measurement results for the first through fourth repetitions are shown in Table 2. Furthermore, a calibration curve obtained by plotting the imidization intensity ratio along the horizontal axis and the etching rate along the vertical axis is shown in FIG. 6.

TABLE 2

| Sample repetition number (repetition) | Cooking time (hours) | Viscosity (Pa·s) | Imidization intensity ratio (-) | Etching rate (μm/minute) |
| --- | --- | --- | --- | --- |
| First repetition | 3.5 | 14.9 | 0.00316 | 0.109 |
| Second repetition | 10 | 4.2 | 0.02014 | 0.086 |
| Third repetition | 12.5 | 2.3 | 0.02812 | 0.067 |
| Fourth repetition | 17.5 | 0.9 | 0.04952 | 0.041 |

[Measurement of Polyimide Dissolution Rate]

A 1 L four-neck flask fitted with a stirrer, a thermometer, a nitrogen gas inlet and a calcium chloride tube was charged with 850 g of N-methyl-2-pyrrolidone (NMP), 57.49 g (0.29 mols) of 4,4'-diaminodiphenyl ether (4,4'-DPE) was added and dissolved, and then 92.51 g (0.29 mols) of 3,3',4,4'-benzophenonetetracarboxylic dianhydride (BTDA) was added, yielding a reaction solution. This reaction solution was stirred for 3 hours at room temperature, yielding a polyamic acid solution.

The temperature of the thus obtained polyamic acid solution was raised to 80° C. using a hot water bath, and when the temperature of the polyamic acid solution reached 80° C., 6 g of ion-exchanged water was added. Subsequently, the polyamic acid solution was reacted for 12 hours at 80° C., thus yielding a polyimide solution. The weight average molecular weight of the polyimide was 75,000.

Measurement of the imidization intensity ratio for the thus obtained polyimide revealed a result of 0.0354. Based on this imidization intensity ratio and the calibration curve obtained above, the polyimide dissolution rate was evaluated at 0.06 (μm/minute).

Example 3

Production of a polyimide was conducted in the manner described below, with the purpose of obtaining a polyimide with an imidization intensity ratio of 0.07 to 0.08 (a dissolution rate of 0.007 to 0.071 μm/minute) and a viscosity of 4.0 to 5.0 Pa·s.

[Polyimide Production]

A 1 L four-neck flask fitted with a stirrer, a thermometer, a nitrogen gas inlet and a calcium chloride tube was charged with 850 g of N-methyl-2-pyrrolidone (NMP), 71.89 g (0.36 mols) of 4,4'-diaminodiphenyl ether (4,4'-DPE) was added and dissolved, and then 78.21 g (0.36 mols) of pyromellitic dianhydride (PMDA) was added, yielding a reaction solution. This reaction solution was stirred for 3 hours at room temperature, yielding a polyamic acid solution.

Figure 7:
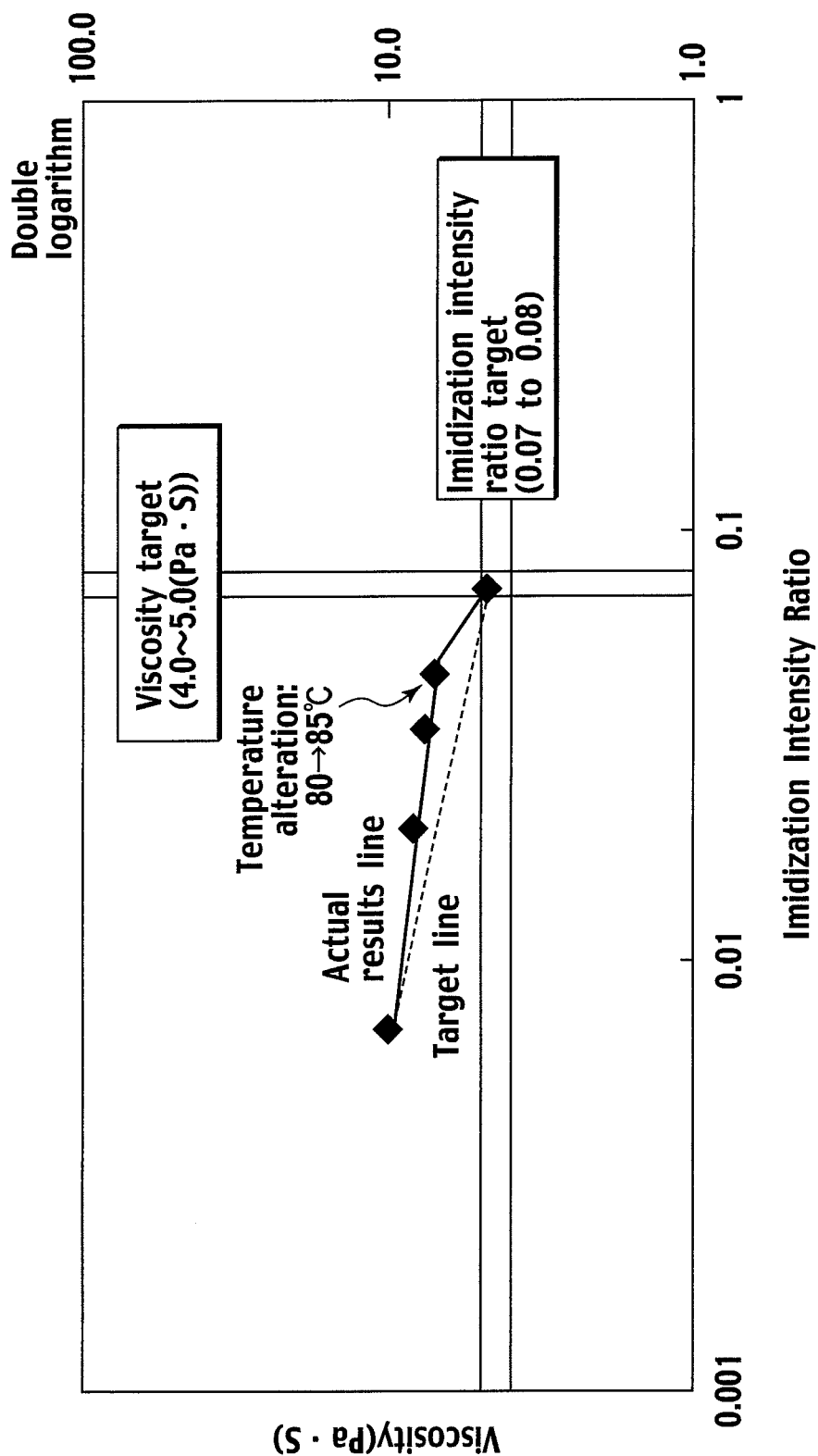
FIG. 7 is a diagram showing the Raman spectral intensity for imide groups and the viscosity in a polyimide production process described in an example 3.

The temperature of the thus obtained polyamic acid solution was raised to 80° C. using a hot water bath, and when the temperature of the polyamic acid solution reached 80° C., 6 g of ion-exchanged water was added. Four hours after the raising of the temperature, the polyimide imidization intensity ratio was 0.00696 and the viscosity was 9.6 Pa·s. FIG. 7 is a graph showing the relationship between the polyimide imidization intensity ratio and the viscosity during the imidization process, wherein the imidization intensity ratio and viscosity target line is shown by a dotted line.

Following reaction for a further 12 hours at 80° C. (total: 16 hours), the polyimide imidization intensity ratio and viscosity were re-measured. The measurement methods used were the same as those described for the example 1. At this point, the polyimide imidization intensity ratio was 0.0463 and the viscosity was 7.2 Pa·s. When these results were plotted on the graph of FIG. 7, it was found that the viscosity deviation, at 15.7%, was not within the viscosity target deviation of 11.1% at this point. Accordingly, the temperature was raised from 80° C. to 85° C., the reaction was continued for a further 6 hours (total: 22 hours), and once again the polyimide dissolution rate and viscosity were measured. The results of these measurements revealed a polyimide imidization intensity ratio of 0.073 (dissolution rate: 0.05 μm/minute) and a viscosity of 4.8 Pa·s, indicating that the target polyimide had been able to be obtained.

The invention claimed is:

1. A method of evaluating a dissolution rate of a polyimide by Raman spectroscopy, wherein a Raman spectral intensity I(a) of imide groups contained within the polyimide is measured, and I(a) is compared with a Raman spectral intensity I(b) of imide groups contained within a polyimide with a known dissolution rate, wherein the polyimides are obtained using an aromatic tetracarboxylic dianhydride and/or an aromatic diamine, and, wherein an intensity ratio $I(a_1)/I(a_2)$ between a Raman spectral intensity $I(a_1)$ of imide groups and a Raman spectral intensity $I(a_2)$ of aromatic rings contained within the polyimide is compared with an intensity ratio $I(b_1)/I(b_2)$ between a Raman spectral intensity $I(b_1)$ of imide groups and a Raman spectral intensity $I(b_2)$ of aromatic rings contained within the polyimide with a known dissolution rate.

2. The method of evaluating a dissolution rate according to claim 1, wherein a correlation equation between an intensity ratio $I(b_1)/I(b_2)$ between a Raman spectral intensity $I(b_1)$ of imide groups and a Raman spectral intensity $I(b_2)$ of aromatic rings contained within the polyimide with a known dissolution rate, and a dissolution rate of the polyimide is used as a calibration curve.

3. The method of evaluating a dissolution rate according to claim 1, wherein the aromatic rings are benzene rings.

4. A method of producing a polyimide, comprising (1) obtaining a polyamic acid using the tetracarboxylic dianhydride and the diamine, and (2) obtaining the polyimide by heating the polyamic acid, wherein an evaluation of dissolution rate is made using the method of evaluating a dissolution rate according to claim 1, and reaction control is conducted based on a result of the evaluation of dissolution rate.

5. A method of producing a polyimide according to claim 4, wherein the evaluation of dissolution rate is conducted on-line or in-line.

6. A method of producing a polyimide according to claim 4, wherein the dissolution rate evaluation is conducted during the process (2), and a heating temperature and/or a heating time is controlled based on a result of the dissolution rate evaluation.

7. A method of producing a polyimide according to claim 6, wherein a viscosity evaluation of the polyimide is conducted during the process (2), and a heating temperature and/or a heating time is controlled based on results of the dissolution rate evaluation and the viscosity evaluation.

8. A method of producing a polyimide, comprising (1) obtaining a polyamic acid using a tetracarboxylic dianhydride and a diamine, (2) obtaining the polyimide by heating the polyamic acid, and (3) evaluating a dissolution rate of the polyimide, wherein, in said evaluating, a Raman spectral intensity I(a) of imide groups contained within the polyimide is measured, wherein I(a) is compared with a Raman spectral intensity I(b) of imide groups contained within a polyimide with a known dissolution rate, wherein the polyimides are obtained using an aromatic tetracarboxylic dianhydride and/or an aromatic diamine, and, wherein an intensity ratio $I(a_1)/I(a_2)$ between a Raman spectral intensity $I(a_1)$ of imide groups and a Raman spectral intensity $I(a_2)$ of aromatic rings contained within the polyimide is compared with an intensity ratio $I(b_1)/I(b_2)$ between a Raman spectral intensity $I(b_1)$ of imide groups and a Raman spectral intensity $I(b_2)$ of aromatic rings contained within the polyimide with a known dissolution rate, and reaction control is conducted based on a result of the measurement of the Raman spectral intensity $I(a)$ of imide groups contained within the polyimide.

9. A method of producing a polyimide according to claim 8, wherein a viscosity of the polyimide is also measured, and reaction control is conducted based on a result of the measurement of the Raman spectral intensity of imide groups and a result of the measurement of viscosity.

10. A method of producing a polyimide according to claim 8, wherein measurement of the Raman spectral intensity of imide groups contained within the polyimide is conducted on-line or in-line.

11. A polyimide obtained by conducting an evaluation using the method of evaluating a dissolution rate according to claim 1.

12. A polyimide obtained by a method of producing a polyimide according to claim 8.

13. A semiconductor device that uses the polyimide according to claim 12.

14. The method of evaluating a dissolution rate according to claim 1, wherein said polyimide with a known dissolution rate is a polyimide having the same repeating units as said polyimide whose dissolution rate is being evaluated.

15. The method of evaluating a dissolution rate according to claim 1, wherein when $I(a)>I(b)$, the dissolution rate of the polyimide being evaluated is slower than that of the polyimide with a known dissolution rate, and wherein when $I(a)<I(b)$, the dissolution rate of the polyimide being evaluated is faster than the dissolution rate of the polyimide with a known dissolution rate.

16. A method of evaluating a dissolution rate of a polyimide by Raman spectroscopy, wherein a Raman spectral intensity $I(a)$ of carboxyl groups within the polyimide is measured, wherein $I(a)$ is compared with a Raman spectral intensity $I(b)$ of carboxyl groups contained within a polyimide with a known dissolution rate, wherein the polyimides are obtained using an aromatic tetracarboxylic dianhydride and/or an aromatic diamine, and, wherein an intensity ratio $I(a_1)/I(a_2)$ between a Raman spectral intensity $I(a_1)$ carboxyl groups and a Raman spectral intensity $I(a_2)$ of aromatic rings contained within the polyimide is compared with an intensity ratio $I(b_1)/I(b_2)$ between a Raman spectral intensity $I(b_1)$ of carboxyl groups and a Raman spectral intensity $I(b_2)$ of aromatic rings contained within the polyimide with a known dissolution rate.

17. A method of producing a polyimide, comprising (1) obtaining a polyamic acid using a tetracarboxylic dianhydride and a diamine, and (2) obtaining the polyimide by heating the polyamic acid, wherein an evaluation of dissolution rate is made using the method of evaluating a dissolution rate according to claim 16, and reaction control is conducted based on a result of the evaluation of dissolution rate.

18. A method of producing a polyimide, comprising (1) obtaining a polyamic acid using a tetracarboxylic dianhydride and a diamine, and (2) obtaining the polyimide by heating the polyamic acid, wherein an evaluation of dissolution rate is made using the method of evaluating a dissolution rate according to claim 1, and reaction control is conducted based on a result of the evaluation of dissolution rate.

19. A polyimide obtained by a method of producing a polyimide according to claim 18.

20. A method of producing a polyimide according to claim 18, wherein a viscosity of the polyimide is also measured, and reaction control is conducted based on a result of the measurement of the Raman spectral intensity of imide groups and a result of the measurement of viscosity.

21. A method of producing a polyimide according to claim 18, wherein measurement of the Raman spectral intensity of imide groups contained within the polyimide is conducted on-line or in-line.

22. A polyimide obtained by conducting an evaluation using the method of evaluating a dissolution rate according to claim 1.

\* \* \* \* \*